United States Patent [19]

Lipton

[11] Patent Number: 5,234,956
[45] Date of Patent: Aug. 10, 1993

[54] METHOD OF PREVENTING NMDA RECEPTOR COMPLEX-MEDIATED NEURONAL DAMAGE

[75] Inventor: Stuart A. Lipton, Newton, Mass.

[73] Assignee: The Children's Medical Center Corporation, Boston, Mass.

[21] Appl. No.: 949,342

[22] Filed: Sep. 22, 1992

Related U.S. Application Data

[63] Continuation of Ser. No. 688,965, Apr. 19, 1991, abandoned.

[51] Int. Cl.$^5$ .......................................... A61K 31/045
[52] U.S. Cl. ................................................... 514/724
[58] Field of Search ........................................ 514/724

[56] References Cited

U.S. PATENT DOCUMENTS 4,806,543  2/1989  Choi .................................. 514/464
5,091,391  2/1992  Aizenman et al. ................. 514/311

FOREIGN PATENT DOCUMENTS

WO91/02810  3/1991  PCT Int'l Appl. .

OTHER PUBLICATIONS

Garthwaite, *Trends in Pharmacological Sciences*, vol. 14, No. 2, pp. 60-67, 1991.
Hope et al., *Proc. Natl. Acad. Sci. USA*, vol. 88, pp. 2811-2814, Apr. 1991.
Meldrum et al., *Trends in Pharmacological Sciences*, vol. 11, pp. 379-387, Sep. 1990.
Garthwaite et al., *Neuroscience*, vol. 26, No. 1, pp. 321-326, 1988.
Merck Index, p. 858.
Merck Index, 9th Edition, pp. 858-859, #6429 and #6429, 1976.
Sucher et al., *Neuropharmacology and Neurotoxicity* 1:29-32, 1990.
Aizenman et al., *Neuron* 2:1257-1263, 1989.
Seubert, *Brain Research* 492:366-370, 1990.
Sernagor, *Neuron.* 2:1221-1227, 1989.
Goldberg et al., *J. Pharm. Exp. Therapeutics* 245:1081-1087, 1988.
Davenport et al., *Eur. J. Pharm.* 154:73-78, 1988.
Choi et al., *J. Pharmacol. and Exp. Therapeutics* 242:713-730, 1987.
Hahn et al., *Proc. Natl. Acad. Sci. USA* 85:6556-6560, 1988.
Choi, *Neuron.* 1:623, 1988.
Rothman et al., *Trends Neurosci.* 10:299, 1987.
Meldrum et al., *Trends Pharm. Sci.* 11:379, 1990.
Weiss et al., *Science* 247:1474, 1990.
Garthwaite et al., *Trends in Neurosciences* 14:60, 1991.
Hope et al., *Proc. Natl. Acad. Sci. USA* 88:2811, 1991.
Aizenman et al., *Neuron* 5:8411-846, 1990.
Majewska et al., *Brain Res.* 537:328-332, 1990.
Levy et al., *Neurosci. Letters* 110:291-296, 1990.

*Primary Examiner*—S. J. Friedman
*Attorney, Agent, or Firm*—Fish & Richardson

[57] ABSTRACT

Disclosed is a method for reducing NMDA receptor-mediated neuronal damage in a mammal by administering to the mammal a nitric-oxide generating compound, or a physiologically acceptable salt thereof, in a concentration effective to cause such reduction. Also disclosed is a method for reducing NMDA receptor-mediated neuronal damage in a mammal by administering to the mammal nitroprusside, nitroglycerin, or a derivative of one of those compounds, in a concentration effective to cause such reduction.

13 Claims, 1 Drawing Sheet

METHOD OF PREVENTING NMDA RECEPTOR COMPLEX-MEDIATED NEURONAL DAMAGE

This is a continuation of application Ser. No. 07/688,965, filed Apr. 19, 1991, now abandoned.

BACKGROUND OF THE INVENTION

This invention relates to the treatment of nervous system disorders, particularly disorders mediated by the N-methyl-D-aspartate (NMDA) subtype of excitatory amino acid receptor complex.

Glutamate has been implicated as a significant factor in the neurotoxicity associated with hypoxic-ischemic encephalopathy, anoxia, hypoglycemia, seizures, trauma, and several degenerative neurological disorders such as the AIDS dementia complex and other neurological manifestations of AIDS, Huntington's disease and Parkinsonism (Hahn et al., *Proc. Natl. Acad. Sci. USA* 85:6556, 1988; Choi, *Neuron* 1:623, 1988; Rothman et al., *Trends Neurosci.* 10:299, 1987; Meldrum et al., *Trends Pharm. Sci.* 11:379, 1990). In many central neurons the predominant form of this neurotoxicity appears to be mediated by activation of the NMDA subtype of glutamate receptor and subsequent influx of excessive $Ca^{2+}$ (Choi, ibid; Weiss et al., *Science* 247:1474, 1990).

SUMMARY OF THE INVENTION

I have discovered that certain compounds protect neurons against NMDA receptor-mediated neuronal damage. Specifically, nitroglycerin, nitroprusside, and their derivatives provide such protection. Thus, one aspect of the invention features a method for reducing NMDA receptor complex-mediated neuronal damage in a mammal, by administering one of the above-described compounds to the mammal.

With regard to the compounds of the first aspect of the invention, I do not wish to bind myself to any particular theory or mechanism of action. However, oxidation of the NMDA receptor is known to protect against NMDA receptor-mediated neuronal damage (see, e.g., PCT W091/02180). It is also known that the active species of nitroglycerin and nitroprusside is nitric oxide (NO) (see, e.g., Garthwaite et al. (*Trends in Neurosciences* 14:60, 1991). Accordingly, one possible mechanism for the protective effect that I have discovered is nitric oxide-induced oxidation of the NMDA receptor-channel complex.

Accordingly, a second aspect of the invention features a method for reducing NMDA receptor complex-mediated neuronal damage by administering a nitric-oxide generating compound, in a concentration effective to cause such reduction. This second aspect of the invention is founded on the premise that NO acts on the NMDA receptor-channel complex to protect against NMDA receptor-mediated damage.

In preferred embodiments of both aspects of the invention, the mammal is a human infected with a virus affecting the nervous system—e.g., measles or human immunodeficiency virus (HIV); and the human manifests symptoms of the AIDS related complex or acquired immunodeficiency syndrome. Alternatively, the mammal has a disorder such as hypoxia, ischemia, hypoglycemia, trauma, seizures or stroke, or is likely to become subject to these, i.e., could be treated prophylactically.

By "NMDA receptor-mediated neuronal damage" is meant any neuronal injury which results from stimulation or costimulation of the NMDA receptor-channel complex, a receptor-channel complex which is found on a subset of mammalian neurons and which includes a molecule that interacts with NMDA or similar agonists (see below) to induce neuron excitation.

By a "nitric oxide-generating compound" is meant any compound which produces a sufficient amount of nitric oxide upon administration to a mammal to reduce neuronal damage or injury.

Useful compounds of the second aspect of the instant invention include any nitric oxide-generating compounds. Verification that a particular compound provides protective oxidation of the NMDA receptor itself is step well understood by those skilled in the art (see, e.g., PCT WO 91/02810). Moreover, applicant notes that the literature describes the enzyme, NO synthase, which produces nitric oxide in certain cell types; this enzyme and its role in neuronal function is discussed in, e.g., Garthwaite et al. (*Trends in Neurosciences* 14:60, 1991) and Hope et al. (*Proc. Natl. Acad. Sci. USA* 88:2811, 1991).

The two preferred compounds of the first aspect of the invention (i.e., nitroglycerin and nitroprusside) provide the advantage of a proven record of safe human administration (i.e., for treatment for cardiovascular disorders).

Disorders which may be treated by the method of the invention include hypoxia, ischemia, hypoglycemia, trauma, seizures, stroke, AIDS dementia and other neurological manifestations of HIV (see, e.g., U.S. Ser. No. 571,949) or other viruses affecting the nervous system, and, generally, acute and chronic neurodegenerative disorders, including, but not limited to Parkinson's disease, Alzheimer's disease, and Huntington's disease.

Regarding compounds according to the second aspect of the invention, the ability of NO to be transported and to cross cell membranes facilitates therapies according to the invention.

. Other features and advantages of the invention will be apparent from the following detailed description and from the claims.

DETAILED DESCRIPTION

The drawings are first briefly described.

DRAWINGS

Figure 1:
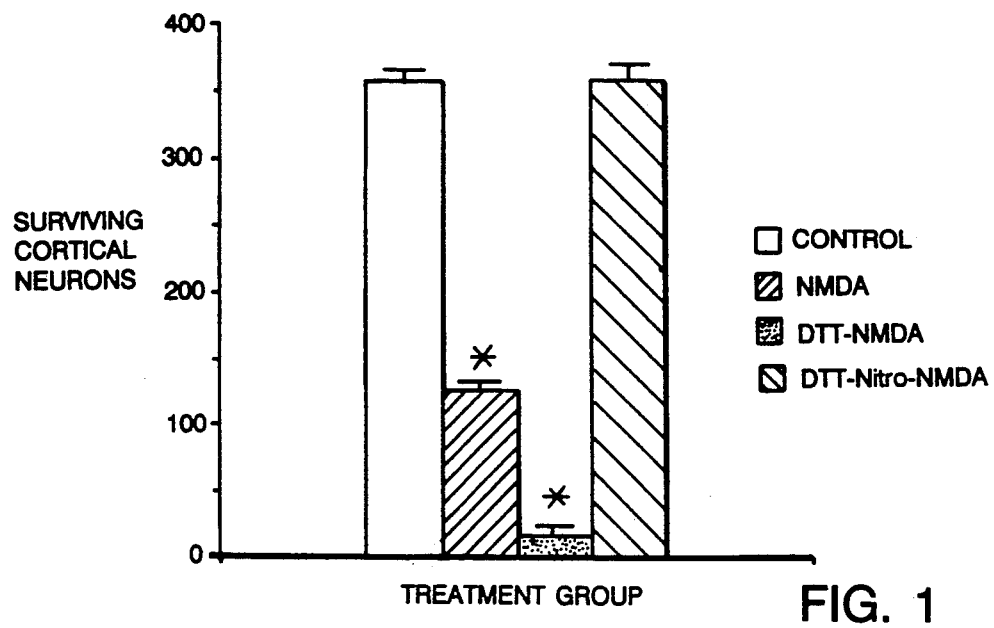
FIG. 1 is a bar graph showing that nitroprusside prevents NMDA-mediated neurotoxicity.

The present invention is based on the finding that the compounds nitroprusside and nitroglycerin reduce NMDA receptor complex-mediated neuronal damage (see below). This reduction in damage may be due to oxidation of the NMDA receptor at the redox modulatory site. The reduction is associated with a decrease in NMDA receptor-operated channel activation by excitatory amino acids (such as NMDA) and a concomitant decrease in intracellular calcium leading to neurotoxicity.

An increased level of one or more glutamate-related compounds is associated with many neurodegenerative disorders (e.g., those listed above). In addition to glutamate itself, neuronal injury may result from stimulation of the NMDA receptor-channel complex by other excitatory amino acids, such as aspartate, quinolinate, homocysteic acid, cysteine sulphinic acid, or cysteic acid, or from stimulation by excitatory peptides, such as N-acetyl aspartyl glutamate.

Nitroglycerin (1,2,3-propanetriol trinitrate or glyceryl trinitrate or GTN), nitroprusside and NO-generating derivatives of either one of those compounds are considered to be particularly useful in the invention.

Compounds of the second aspect of the invention (i.e., nitric oxide-generating compounds and their derivatives) may be tested for efficacy in reducing neuronal damage using the assays described below—i.e. in assays of NMDA evoked ionic current (see, e.g., PCT WO 91/02810), in assays of NMDA-evoked increases in intracellular $Ca^{2+}$ (see below), or in assays of neuronal cell death (see below). An effective compound will cause a decrease in ionic current, intracellular $Ca^{2+}$ concentration, or in neuronal cell death, respectively. Compounds most preferred in the invention are those which effect the greatest protection of neurons from NMDA receptor complex-mediated injury e.g., that injury resulting from stimulation of the NMDA receptor by NMDA(as shown below) or other excitatory amino acids or stimulation by excitatory peptides, such as N-acetyl aspartyl glutamate.

ASSAY FOR NEURONAL CELL FUNCTION AND DEATH

To test compounds for their ability to prevent neurotoxicity, neuronal cell death may be assayed as follows. Neonatal cortical neurons were prepared according to the general method of Snodgrass et al. (1980) Brain Res. 190:123-138; and Rosenberg et al (1988) J. Neurosci. 8:2887-2899. Cultures are monitored following a brief exposure (5 minutes) to 100 μM NMDA, or to 5 mM DTT (for 5 minutes) followed by 100 μM NMDA (for 5 additional minutes), and overnight incubation (i.e., 16 to 24 hours). Experiments in vivo suggest that a transient reducing state exists in the brain following stroke; the introduction of the chemical reducing agent DTT may mimic this reducing environment, increasing the similarity of the in vitro assay to the in vivo situation. The candidate compound is tested by addition (e.g., in a series of concentrations ranging from 0.1 nM-10 mM) after DTT treatment but before NMDA treatment. Incubations last 16-24 h at 37° C. in an atmosphere of 5% $CO_2$/95% air. Neuronal cultures are scored for cell survival after overnight incubation because NMDA toxicity is often delayed by several hours following NMDA exposure. The ability of cortical neurons to maintain phase-bright appearance and exclude trypan blue is used as an index of survival (Rosenberg et al., Neurosci. Lett. 103: 162-168, 1989).

A compound may be tested for utility in the method of the invention using any type of neuronal cell from the central nervous system, as long as the cell can be isolated intact by conventional techniques. Although cortical neuron cultures are used above, retinal ganglion cell neurons, spinal cord neurons, cerebellar granular neurons, or any neuron containing NMDA receptors (e.g., neurons from other regions of the cortex) may also be used. Such neurons may be prenatal or postnatal.

There now follows an example of a compound useful in the method of the invention and an illustration of its efficacy in reducing neuronal damage. This example is provided to illustrate the invention and should not be construed as limiting.

NITROPRUSSIDE PREVENTS NMDA RECEPTOR-MEDIATED NEUROTOXICITY

Using the assay described above, the compound nitroprusside was tested for its ability to increase survival of neonatal cortical neurons. The neuronal cells were incubated for 16-24 hours at 37° C. in a humidified atmosphere of 5% $CO_2$ and 95% air.

As shown in FIG. 1, brief treatment (5 minutes) with NMDA (100 μM) produced significant neuronal cell neurotoxicity (P < 0.01, indicated by an asterisk) after overnight incubation [compare FIG. 1, column 1 (untreated control neurons) and column 2 (neurons treated with NMDA)]. A 5 minute exposure to 0.5 mM DTT (prior to the brief treatment with NMDA) further increased neurotoxicity [compare FIG. 1, column 2 (neurons treated with NMDA) with column 3 (neurons treated with DTT followed by NMDA)]. In additional cultures, nitroprusside was added for 5 minutes (after DTT exposure but prior to NMDA treatment) to the growth media to a final concentration of 1 μM-1 mM. Nitroprusside prevented neuronal cell death resulting from the combination of NMDA and DTT [compare FIG. 1, column 3 (neurons treated with DTT followed by NMDA) with column 4 (neurons treated with DTT followed by nitroprusside followed by NMDA)]. Increased neuronal survival at 1 mM nitroprusside (FIG. 1, column 4) reached statistical significance compared to the control (FIG. 1, column 1). An analysis of variance was used to test for significance; this analysis was followed by a Sheffé test for multiple comparison of means (Hahn et al., 1988, supra). Doses of nitroprusside as low as 0.1 nM are expected to have neuroprotective effects.

MEASUREMENT OF INTRACELLULAR $CA^{2+}$

The concentration of intracellular free $Ca^{2+}$ ([$Ca^{2+}$]i) is measured in neonatal cortical neurons by digital imaging microscopy with the $Ca^{2+}$ sensitive fluorescent dye fura 2 as follows. The same cortical neuronal cultures as described above are used. During $Ca^{2+}$ measurements, unless otherwise stated the fluid bathing the neurons consists of Hanks' balanced salts: 137.6 mM NaCl, 1 mM $NaHCO_3$, 0.34 mM $Na_2HPO_4$, 0.44 mM $KH_2PO_4$, 5.36 mM KCl, 1.25 mM $CaCl_2$, 0.5 mM $MgSO_4$, 0.5 mM $MgCl_2$, 5 mM Hepes NaOH, 22.2 mM glucose, and phenol red indicator (0.001% v/v); pH 7.2. NMDA and other substances are usually applied to the neurons by pressure ejection after dilution in this bath solution. Neuronal [$Ca^{2+}$]i is analyzed with fura 2-acetoxy-methyl ester (AM) as described [Grynkiewicz, et al., J. Biol. Chem. 260:3440 (1985); Williams et al., Nature 318:558 (1985); Connor et al., J. Neurosci. 7:1384 (1987); Connor et al., Science 240:649 (1988); Cohan et al., J. Neurosci. 7:3588 (1987); Mattson, et al., ibid, 9:3728 (1989)]. After adding Eagle's minimum essential medium containing 10 μM fura 2-AM to the neurons, the cultures are incubated at 37° C. in a 5% $CO_2$/95% air humidified chamber and then rinsed. The dye is loaded, trapped, and deesterified within 1 hour, as determined by stable fluorescence ratios and the effect of the $Ca^{2+}$ ionophore ionomycin on [$Ca^{2+}$]i is measured. During $Ca^{2+}$ imaging, the cells are incubated in a solution of Hepes-buffered saline with Hanks' balanced salts. The [$Ca^{2+}$]i is calculated from ratio images that are obtained by measuring the fluorescence at 500 nm that is excited by 350 and 380 nm light with a DAGE MTI 66 SIT or QUANTEX QX-100 Intensified CCD camera mounted on a Zeiss Axiovert 35 microscope. Exposure time for each picture is 500 ms. Analysis is performed with a Quantex (Sunnyvale, Calif.) QX7-210 image-processing system. Since cells are exposed to ultraviolet light only during data collection (generally less than a total of 20 s per cell), bleaching of fura 2 is minimal.

NITROPRUSSIDE DECREASES THE NMDA-MEDIATED INCREASE IN THE INTRACELLULAR CONCENTRATION OF $CA^{2+}$

Figure 2:
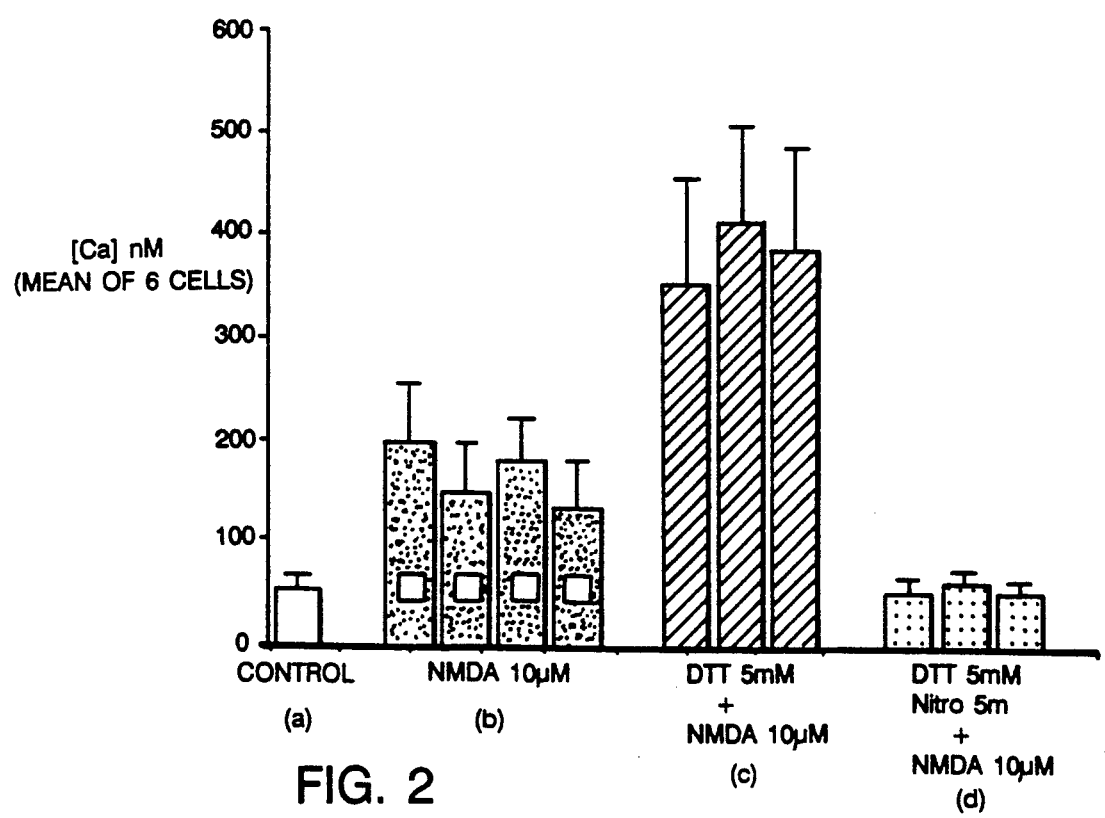
FIG. 2 is a bar graph of intracellular $Ca^{2+}$ concentration (i.e., $[Ca^{2+}]i$) in (a) control cells and in the presence of (b) NMDA alone, (c) NMDA after dithiothreitol (DTT), and (d) NMDA after DTT and nitroprusside.

NMDA-receptor mediated neurotoxicity has been shown to involve an increase in intracellular $Ca^{2+}$ concentration. The increase in $[Ca^{2+}]i$ was documented in the following experiment. Intracellular $Ca^{2+}$ was measured as described above. Application of 10 μM NMDA produced a striking increase in $[Ca^{2+}]i$ [FIG. 2, columns 2-5(b)]. Compared to control levels [$Ca^{2+}=50$ nM Col. 1(a)]obtained before the addition of NMDA, levels following NMDA addition increased to 200 nM. These results represent the average $[Ca^{2+}]i$ measurement of six independent neurons measured every two minutes for four trials. Using the same neurons, the $[Ca^{2+}]i$ was allowed to return to the control level, and the cultures were treated first with 5 mM DTT for 5 minutes (and washed out) and then 10 μM NMDA was applied repeatedly. This combined DTT and NMDA treatment produced an increase in $[Ca^{2+}]i$ levels which was even greater than that observed for NMDA treatment alone; specifically, an average level of 400 nM free calcium ion concentration was measured. These results are shown in columns 6-8 (c) and represent the average measurement for the same six neurons measured every two minutes for three trials. Calcium levels were again allowed to return to control levels and the effect of nitroprusside on $[Ca^{2+}]i$ was tested in the same neurons whose NMDA receptors had been previously chemically reduced with 5 mM DTT. Following treatment with 5 mM nitroprusside for 5 minutes (and wash out), 10 μM NMDA did not evoke as great a $Ca^{2+}$ response. Indeed, the free calcium ion concentration was very similar to that observed in control cultures (approximately 50 nM averaged for the three trials at two minute intervals for the same six neurons). These results are shown in columns 9-11 (d).

Verification that the effect at issue involves the NMDA redox site can be provided as follows.

Maximal chemical reduction of the site by 0.5-5 mM dithiothreitol (DTT) prior to nitroprusside treatment increases NMDA responses (i.e., NMDA produces an increased intracellular calcium concentration (in part via ionic current) and neuronal death), but nitroprusside (0.3-5 mM) prevents these effects. Pretreatment with a strong oxidizing agent 5-5-dithio-bis-2-nitrobenzoic acid (DTNB, 0.1-2 mM, administered in a parallel experiment in place of DTT) blocks the effect of nitroprusside on NMDA evoked maximum $[Ca^{2+}]i$ increase and ionic current increase, although NMDA itself still maintains some effect. In other words, a maximal chemical oxidation with DTNB abrogates the effect of nitroprusside, strongly suggesting that nitroprusside is acting in the same manner under these conditions (i.e., as an oxidizing agent) because it has no further effect after DTNB oxidation of the redox modulatory site of the NMDA receptor-channel complex. It should be noted that once the redox modulatory site is oxidized or reduced, even after subsequent wash out of the redox agent, the site remains in this state until another effective redox agent is introduced.

THERAPY

To prevent neuronal damage, compounds of the invention may be administered by any of a number of routes in an amount sufficient to attenuate an NMDA-evoked ionic current or a rise in $[Ca^{2+}]i$, or neurotoxicity. The compound may be included in a pharmaceutical preparation, using a pharmaceutical carrier (e.g., physiological saline); the exact formulation of the therapeutic mixture depends upon the route of administration. Preferably, the compound is administered orally or intravenously, but it may also be administered sublingually, by spray, by transdermal patch, or by ointment. The preferred compounds, nitroglycerine or their derivatives (including all those preparations commercially available, e.g., those listed in the *Physician's Desk Reference* (1991) under coronary vasodilators or under nitroglycerin or nitroglycerin intravenous and including isosorbide mononitrate, isosorbide dinitrate, nitroglycerin sublingual, NT-1, Niotrocor, Nitroderm, Nitrodisc, Nitro-dur, Nitro-Dur II, Nitrofilm, Nitrogard, Nitroglin, Nitropen, Tridil, and 6-chloro-2-pyridylmethyl nitrate) are administered at 0.01-1000 mg/day, in divided doses. Sodium nitroprusside—$Na_2[Fe(CN)_5NO]\cdot 2H_2O$ (from Elkins-Sinn, Inc., Cherry Hill, N.J.) or Nipride (from Roche, Nutley, N.J.)—are administered intravenously at 0.5-10 μg/min. Other nitric oxide-generating compounds, determined to be an effective neuroprotective agent by the assays described herein, is administered orally, intravenously, sublingually, by spray, or by transdermal patch or ointment at a dosage suitable to reduce neuronal damage, or NMDA evoked ionic current or increased $[Ca^{2+}]i$. Generally, such compounds are administered in dosages of 0.1-5 mg/day in divided doses. Treatment may be repeated as necessary to prevent or alleviate neurological injury. The compounds of the invention can be utilized to protect against a number of neurotoxic disorders caused by elevated levels of glutamate or related compounds. Such neurotoxic disorders include ischemia, hypoxia, hypoglycemia, trauma, epilepsy, Huntington's disease, and Alzheimer's disease and other neurodegenerative disorders. The method of the invention is particularly preferred for the treatment of AIDS dementia and other neurological manifestations of the AIDS virus. The method may also be used for reduction of neuronal damage resulting from infection with other viruses which cause damage to the nervous system.

OTHER EMBODIMENTS

The method described herein is useful for reducing neuronal injury in any mammal having NMDA receptors. Treatment of neuronal damage in humans is the preferred utility; but the method may also be employed successfully for veterinary purposes.

I claim:

1. A method for reducing NMDA receptor-mediated neuronal damage in a human comprising reducing the NMDA-mediated increase in the intraneuronal concentration by administering to said human a compound selected from the group consisting of: a) nitroprusside, b) nitroglycerin, c) an NO-generating derivative of nitroprusside or nitroglycerin, or d) a physiologically acceptable salt of a)-c), above, in a concentration effective to cause such reduction.

2. The method of claim 1, wherein said compound is nitroprusside or a physiologically acceptable salt thereof.

3. The method of claim 1, wherein said compound is nitroglycerine or a physiologically acceptable salt thereof.

4. The method of claim 1, wherein said compound is nitroprusside or an NO-generating derivative thereof.

5. The method of claim 1, wherein said compound is nitroglycerin or an NO-generating derivative thereof.

6. The method of any of claims 1-5, wherein said human is infected with a human immunodeficiency virus.

7. The method of claim 6, wherein said human manifests symptoms of the AIDS related complex or acquired immunodeficiency syndrome.

8. The method of any of claims 1-5 wherein said human suffers from a disorder selected from the group consisting of hypoxia, ischemia, trauma, hypoglycemia, seizures, stroke, Alzheimer's disease, Huntington's disease, or Parkinson's disease.

9. A method for controlling neuronal damage associated with a disorder selected from the group consisting of hypoxia, ischemia, trauma, hypoglycemia, seizures, stroke, Alzheimer's disease, Huntington's disease, Parkinson's disease, and infection with Human Immunodeficiency Virus (HIV), said method comprising administering to a patient: a) nitroglycerin, b) nitroprusside, c) an NO-generating derivative of a) or b), or d) a physiologically acceptable salt of a)-c).

10. The method claim 9 wherein said disorder is infection with HIV.

11. The method claim 9 wherein said disorder is hypoxia or ischemia.

12. The method of claim 9, claim 10 or claim 11 comprising administering nitroglycerin or a physiologically acceptable salt thereof to said patient.

13. The method of claim 9, claim 10 or claim 11 comprising administering nitroprusside or a physiologically acceptable salt thereof to said patient.

* * * * *

UNITED STATES PATENT AND TRADEMARK OFFICE
CERTIFICATE OF CORRECTION

PATENT NO. : 5,234,956
DATED : AUGUST 10, 1993
INVENTOR(S) : STUART A. LIPTON

It is certified that error appears in the above-identified patent and that said Letters Patent is hereby corrected as shown below:

At column 1, line 7, before "BACKGROUND OF THE INVENTION" insert --This invention was made with government support under Grant No. R01 EY05477 by the NIH. The government has certain rights in the invention.--

Signed and Sealed this

Twenty-sixth Day of September, 2000

Attest:

Q. TODD DICKINSON

*Attesting Officer*      *Director of Patents and Trademarks*